United States Patent [19]
Yamaguchi

[11] 4,261,345
[45] Apr. 14, 1981

[54] ENDOSCOPE CONNECTOR

[75] Inventor: Tatuya Yamaguchi, Kokubunji, Japan

[73] Assignee: Olympus Optical Co., Ltd., Tokyo, Japan

[21] Appl. No.: 96,008

[22] Filed: Nov. 20, 1979

[30] Foreign Application Priority Data

Nov. 20, 1978 [JP] Japan .................................. 53/143130

[51] Int. Cl.³ .............................................. A61B 1/00
[52] U.S. Cl. ...................................................... 128/6
[58] Field of Search ............................ 128/6, 4, 7–11, 128/247

[56] References Cited
U.S. PATENT DOCUMENTS

| | | | |
|---|---|---|---|
| 3,726,272 | 4/1973 | Fukami et al. | 128/6 |
| 4,188,942 | 2/1980 | Fehlberg | 128/6 |

FOREIGN PATENT DOCUMENTS 49-54127 5/1974 Japan ........................................... 128/6
52-25036 6/1977 Japan ........................................... 128/6

Primary Examiner—John D. Yasko

[57] ABSTRACT

An endoscope connector comprises a cylindrical body detachably connected to a light source console and provided with an illumination optical fiber bundle and a fluid passage, an annular grooved communication chamber formed in the outer peripheral wall of the connector body to communicate with the fluid passage, a ring member rotatably surrounding the communication chamber in a fluid tightness, and a fluid-guiding fitting mounted on the ring member. Application of the ring member in combination with the annular grooved communication chamber reduces a length of time required to free a protective tube for coupling the connector to the endoscope from twistings which probably arise from the unavoidable rotation of the endoscope during insertion into a coeliac cavity, thereby decreasing the operation time of the endoscope.

8 Claims, 7 Drawing Figures

ENDOSCOPE CONNECTOR

BACKGROUND OF THE INVENTION

This invention relates to a connector for coupling the operation section of an endoscope to a light source console set outside thereof.

The operation section 1 of an endoscope is generally connected, as shown in FIG. 1, to a flexible protective tube 2 covering a power supply cord, illumination optical fiber bundle, gas feed tube, a water feed tube and a fluid-suction tube. Fitted to the outer end of the protective tube 2 is a connector 3 which is coupled to a light source device, gas feed tube, water feed tube and fluid-suction type. By the connector 3 electric power and illumination light are supplied to the operation section of the endoscope and a fluid is fed to and withdrawn from the operation section.

The conventional connector 3 has its outer end portion fitted, as shown in FIG. 2, with a plurality of connection terminal pins 4, a light guide tube 5 and a water inlet 10 all axially protruding from the end face of the connector 3, and a water inlet fitting 6 and fluid outlet fitting 7 both projecting outward crosswise of the peripheral wall of said end portion of the connector 3. In practical application, the connector 3 is put into the socket 9 of a light source console 8. The connection pins 4 are connected to a power source. The light guide tube 5 is connected to a light source in the console 8. The gas inlet 10 is connected to a gas outlet. A water feed tube is attached to a water inlet fitting 6, and a fluid-suction tube is connected to a fluid outlet fitting 7. Thus, the connector 3 is nonrotatably fitted to the light source console 8. Where, therefore, an endoscope such as a colonofiberscope is inserted into a coeliac region, for example, an intricately twisted large intestine, the endoscope has to be rotated many times about its axis to effect its smooth passage through the intestine. Consequently the protective tube 2 is also frequently twisted, probably resulting in the damage of the members contained in the protective tube 2 such as an optical fiber bundle, and gas feed, water feed and fluid-suction tubes. The customary practice to eliminate the above-mentioned difficulties is to pull the connector 3 from the socket 9 of the light source console 8 to relieve the connector 3 from its twistings and again put the connector 3 into the socket 9. Where the connector 3 is to be freed of its twistings, the water feed tube and fluid-suction tube have to be withdrawn beforehand from the corresponding water inlet fitting 6 and fluid outlet fitting 7. After the connector 3 is cleared of its twistings, the water feed and fluid-suction tubes have to be inserted into the water inlet fitting 6 and fluid outlet fitting 7, respectively. Consequently, the prior art endoscope connector had the drawback that the operation of an endoscope using such connector involved unnecessary work and idle time.

SUMMARY OF THE INVENTION

The object of this invention is to provide an endoscope connector, wherein a ring is rotatably mounted on the connector put into the socket of a light source console, and fittings for tubes are fitted to the ring, thereby enabling an optical fiber bundle to be relieved from its twistings without removing the tubes and consequently elevating the operating efficiency of an endoscope.

This invention provides an endoscope connector which comprises a cylindrical connector body which can be detachably connected to a light source console and through which an illumination optical fiber bundle and fluid guide means extend, at least one annular grooved communication chamber which is formed in the outer peripheral wall of the cylindrical connector body and with which the fluid guide means communicate, a ring member rotatably surrounding the annular grooved communication chamber in a fluid tightness, and fluid guide fitting mounted on the ring member.

BRIEF DESCRIPTION OF THE DRAWINGS

This invention can be fully understood from the following detailed description with reference to the accompanying drawings, in which.

DETAILED DESCRIPTION OF THE PREFERRED EMBODIMENTS

Figure 3:
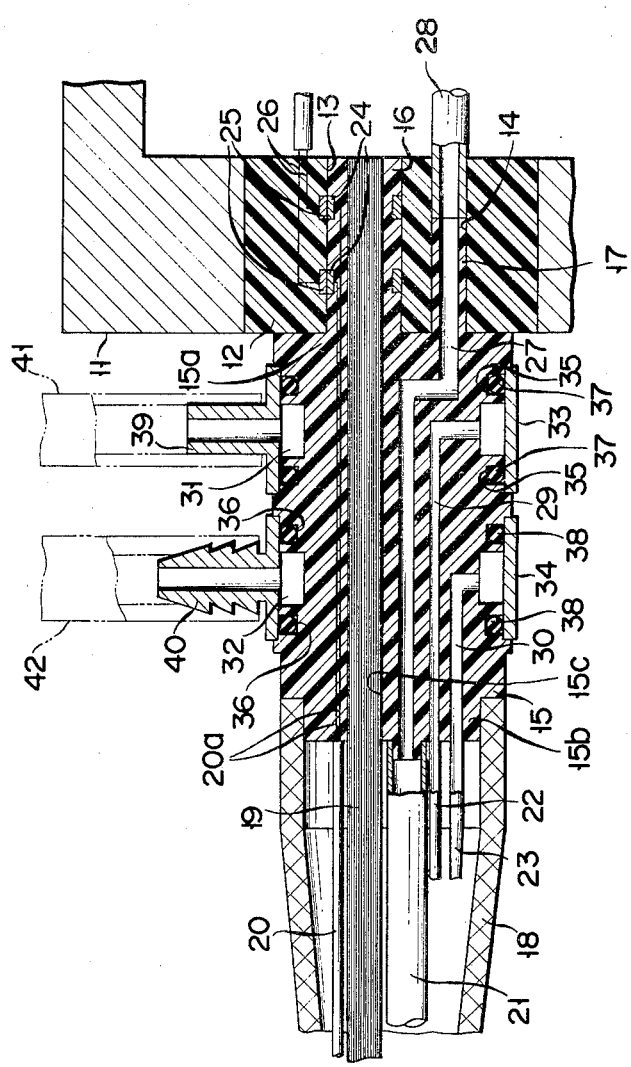
FIG. 3 is a longitudinal cross-sectional view of an endoscope connector embodying this invention.

Referring to FIG. 3, a socket section 12 prepared from plastic material or any other electric nonconductor is provided in the front wall of a light source console. This socket section 12 is penetrated by two parallel holes 13, 14.

One end 15a of a cylindrical connector body 15 which is made of electrically non-conductive material such as polytetrafluoroethylene is provided with plugs 16, 17 which are inserted into the corresponding holes 13, 14 of the socket section 12. The other end 15b of the connector body 15 is connected to one end of a flexible protective tube 18, the other end of which is connected to the operation section of an endoscope.

An illumination optical fiber bundle 19, an electric cord 20, a gas feed tube 21, a liquid feed tube 22 and a fluid-suction tube 23 are extended from said one end 15a of the connector body 15 through the protective tube 18. The illumination optical fiber bundle 19 penetrates a hole 15c formed longitudinally throughout the connector body 15 up to the free end of the plug 16 to face the light source in the light source console 11.

The wires 20a included in the electric cord 20 extend through the connector body 15 in parallel with the illumination optical fiber bundle 19 to be connected to electric contacts 24 annularly arranged on the outer peripheral wall of the plug 16. Electric contacts 25 are provided on the inner wall of the hole 13 of the socket section 12, into which the plug 16 is inserted, thereby effecting contact with the corresponding electric contacts 24. Wires 26 led out of the electric contacts 25 are connected to an electric power source through the console 11.

The gas feed tube 21 is connected at said one end 15a of the connector body 15 to a gas feed passage 27 extended through the connector body 15 and longitudinally penetrating the plug 17. The gas feed passage 27 is connected to a gas feed pump (not shown) disposed, for example, in the light source console 11 through a connection tube 28, one end of which is inserted into the plug 17. The above-mentioned arrangement enables, for example, air, carbon dioxide or nitrous oxide gas to be conducted into a coeliac region such as the large intestine through the gas feed passage 27, the gas feed tube 21 and the endoscope channel.

The liquid feed tube 22 and the fluid-suction tube 23 are connected to a liquid feed passage 29 and a fluid-suction passage 30 which extend in the connector body 15 to said one end 15a thereof. Those end portions of the liquid feed passage 29 and the fluid-suction passage 30 which are in the connector body 15 communicate with corresponding annular communication chambers 31, 32 comprising annular grooves formed in the peripheral wall of the connector body 15.

Ring member 33, 34 each made wider than the corresponding annular communication chambers 31, 32 are so mounted on the connector body 15 as to fully cover the communication chambers 31, 32 and to be rotatable but immovable in the axial direction.

Annular grooves 35, 36 are formed in those portions of the outer peripheral wall of the connector body 15 which are positioned adjacent to both edges of the respective communication chambers 31, 32. O-rings 37, 38 are respectively fitted into the annular grooves 35, 36. The O-rings 37, 38 contact the inner walls of the ring members 33, 34 to seal the outer peripheral wall of the connector body 15 and the inner walls of the ring members 37, 38 in a fluid tightness.

The ring member 33 is fitted with a liquid feed fitting 39, and the ring member 34 with a fluid-suction fitting 40. The liquid feed fitting 39 caused the communication chamber 31 to communicate with a liquid feed pump (not shown) through a connection tube 41, thereby conducting a liquid such as distilled water, physiological salt solution, medicinal liquid or warm water into a coeliac region, for example, the large intestine through the liquid feed passage 29, the liquid feed tube 22 and the endoscope channel. The fluid-suction fitting 40 causes the communication chamber 32 to communicate with a suction pump (not shown) through a connection tube 42, thereby enabling coeliac blood, viscous liquid or gas or a medicinal liquid which has served the purpose all to be sucked out through the endoscope channel, fluid-suction tube 23 and fluid-suction passage 30.

The endoscope connector comprises the connector body 15, ring members 33, 34 mounted thereon, and liquid feed fitting 39 and fluid-suction fitting 40 attached to the corresponding ring members 33, 34.

In operation, where the connector body 15 is fitted, as shown in FIG. 3, into the socket 12 of the light source console 11, and an endoscope, for example, a colonofiberscope (an endoscope for large intestine) is inserted into a coeliac region such as the large intestine, which is intricately bent, the endoscope is rotated many times about its axis, probably resulting in the twisting of the protective tube 18. If, in this case, the protective tube 18 is excessively distorted, damage will occur, as previously described, in the illumination optical fiber bundle 19, electric cord 20, gas feed tube 21, liquid feed tube 22, fluid-suction tube 23 and, in some cases, the protective tube 18 itself, leading to the failure of the endoscope to be rotatingly guided into a coeliac cavity.

To avoid the above-mentioned difficulties, the connector body 15 is pulled out of the socket 12, and then rotated in a direction opposite to that in which the protective tube 18 is twisted to relieve it from its twistings. Thereafter the connector body 15 is fitted into the socket 12. The ring members 33, 34 are freely rotatable relative to the connector body 15. Where, therefore, the liquid feed fitting 39 and fluid-suction fitting 40 are held by hand during the rotation of the connector body 15 to free the protective tube 18 from its twistings, these fittings 39, 40 are not rotated with the connector body 15, thus completely eliminating the necessity of removing the connection tubes 41, 42 from the corresponding fittings 39, 40. Therefore, the endoscope connector of this invention offers the advantages that it is possible to save work and time required to take off the connection tubes from the fittings as is the case with the prior art endoscope connector, before relieving the protective tube from its twistings and thereafter again attaching the connection tubes to the fittings; and the endoscope can be operated with greater ease than has been possible in the past and a length of time required to examine, the physiological condition of, for example, a patient can be reduced, thereby ensuring the safe operation of an endoscope by the operator and alleviating a patient's pains.

Figure 4:
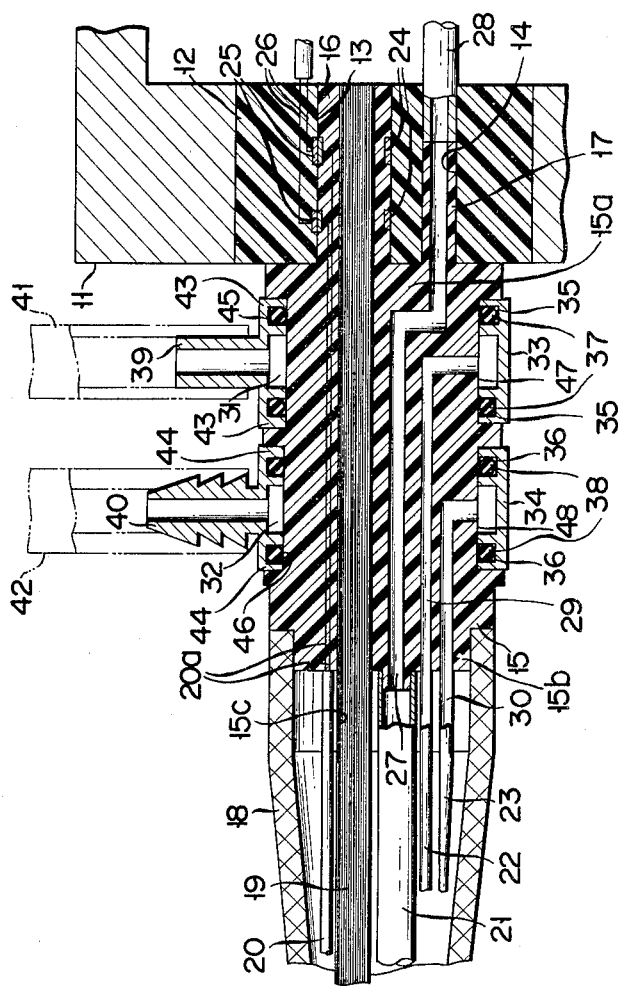
FIGS. 4 and 5 are the longitudinal cross-sectional views of endoscope connectors according to other embodiments of this invention.
Figure 7:
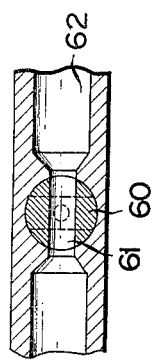
FIG. 7 shows an embodiment of a coke valve used with the embodiment of the endoscope connector indicated in FIG. 6.

With the endoscope connector according to the embodiment of FIG. 4, ring members 33, 34 are substantially as wide as corresponding annular communication chambers 31, 32. A pair of flanges 43 and a pair of flanges 44 extending radially inward are provided on both edge portions of the corresponding annular communication chambers 31, 32. The flanges 43, 44 are respectively provided with annular grooves 45, 46 into which O-rings 37, 38 are fitted. The O-ring 37, 38 contact the bottoms 47, 48 of the annular communication chambers 31, 32 for sealing. The embodiment of FIG. 4 is substantially the same as that of FIG. 3 in respect of the other arrangements than described above, and operation and effect. The parts of FIG. 4 the same as those of FIG. 3 are denoted by the same numerals, description thereof being omitted.

Figure 5:
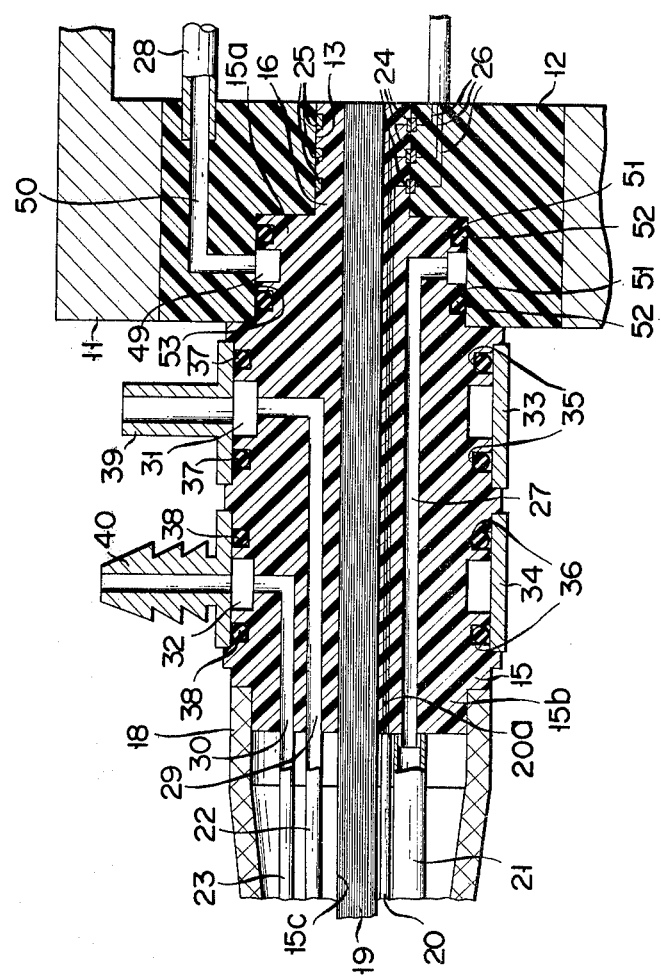

In the embodiment of FIG. 5, the plug 17 used in FIGS. 3 and 4 is omitted. Instead, that portion of the connector body 15 which lies adjacent to one end 15a is thinner than the other portions of the connector body 15. The outer peripheral wall of the narrower portion of the connector body 15 is provided with an annular communication chamber 49 for communication with a gas feed passage 27. Formed in a socket portion 12 of a light source console 11 is a connection passage 50, one end of which communicates with the communication chamber 49, and the other end of which communicates with a connection tube 28. O-rings 52 fitted into annular grooves 51 formed in those parts of the narrower section of the connector body 15 lying adjacent to said one end 15a thereof which are positioned adjacent to both edges of the annular communication chamber 49 contact the inner wall of a hole 53 having substantially the same inner diameter as the narrower section of the connector body 15 to seal the annular communication chamber 49. With the embodiment of FIG. 5, the electric cord 20 includes three wires 20a. There are also provided three contact rings 24, three contact pieces 25 and three wires 26. These wires 22a, 26 are used to transmit electric power to a film takeup motor for an endoscope camera, and also to supply a synchronizing electric signal for a shutter release at the time of photographing and a light quantity signal for automatic control of exposure time. The three wires 22a and the three wires 26 are obviously applicable to the embodiments of FIGS. 3 and 4. The members 20a, 24, 25, 26 need not be provided in a limited number of 3. Obviously they may be used in a number of 2 or 4 or over. The other arrangement of the embodiment of FIG. 5 than described above in the same as that of the embodiment of FIG. 3. The construction of the ring member used in the embodiment of FIG. 4 is applicable to the embodiment of FIG. 5.

The embodiment of FIG. 5 is not provided with a gas feed plug, but only with a plug 16 for the illumination optical fiber bundle. Unlike the embodiments of FIGS. 3 and 4, therefore, the plug 16 can be freely rotated in the hole 13. The embodiment of FIG. 5 has the advantages that the connector body 15 can be rotated with the endoscope, completely eliminating the necessity of pulling the connector body 15 from the socket section 12 to prevent the distortion of the protective tube 18; and consequently it is possible to completely save idle time which was unavoidably consumed with the prior art endoscope connector to relieve the protective tube 18 from its twistings or reduce the idle time as much as possible.

Figure 1:
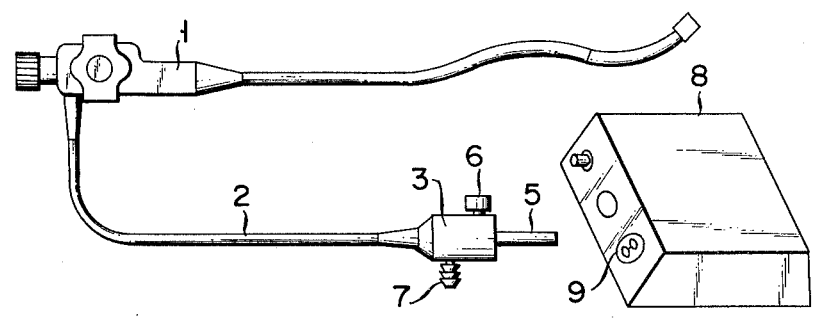
FIG. 1 is an oblique view of the whole of the prior art endoscope.
Figure 2:
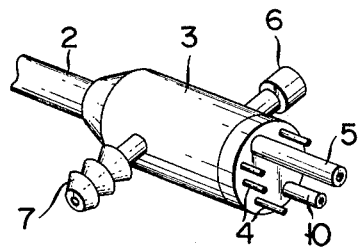
FIG. 2 is an oblique view of the prior art endoscope connector.
Figure 6:
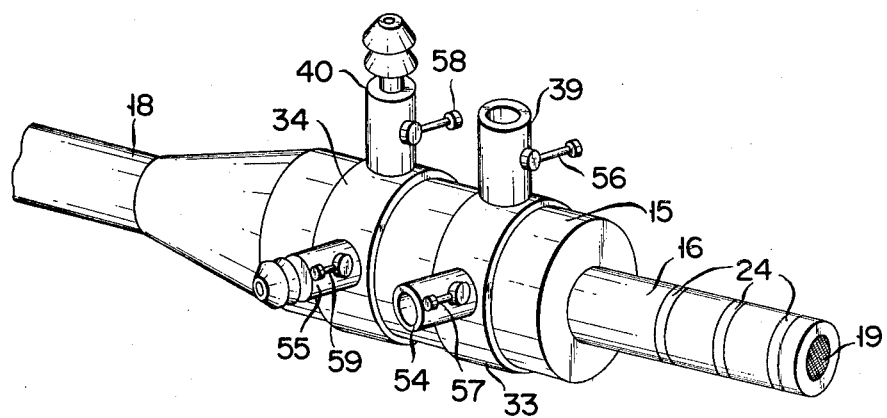
FIG. 6 is an oblique view of an endoscope connector according to a further embodiment of the invention.

With an endoscope connector according to the embodiment of FIG. 6, ring member 33 is provided with a pair of fittings 39, 54, and the ring member 34 similarly with a pair of fittings 40, 55. Provided in the fittings 39, 54, 40, 55 are cock valves which are operated by the corresponding levers 56, 57, 58, 59. The cock valve may be the type provided with a penetrating hole 61 as shown by reference numeral 60 in FIG. 6. With the embodiment of FIG. 6, the penetrating hole 61 is aligned with the passage 62 of the respective fittings 39, 54, 40, 55 to cause a fluid to run through the passage 62. Or the penetrating hole 61 is set perpendicular to the passage 62 as indicated in broken lines, thereby closing the passge 62 with the cock valve 60.

The above-mentioned arrangement enables two types of fluid to be conducted into a coeliac cavity selectively through either of the separate fittings 39, 54 or a fluid remaining in the coeliac cavity to be drawn off in two separate streams through the fittings 39, 54. The embodiment of FIG. 6 has the advantages that where it is necessary to take a fluid into or out of the coeliac cavity in two streams, the work of removing a connection tube from the corresponding fitting and thereafter fitting the connection tube thereto again can be omitted, thereby shortening the operation time of an endoscope; and since it is possible to use, for example, the fitting 39 for the influx of a fluid and, for example, the fitting 54 for the introduction of a gas, the fluid feed tube and fluid feed passage used in the embodiments of FIGS. 3 to 5 can be omitted, thereby simplifying the internal construction of the endoscope connector.

What is claimed is:

1. In an endoscope comprising:
    an operation section;
    a protective tube having two ends, one end being connected to the operation section;
    a connector comprising a cylindrical connector body, one end of which is detachably connected to a light source console set outside of the endoscope, and the other end of which is connected to the other end of the protective tube, and in which at least one fluid-guiding passage is provided, said connector body having an outer peripheral wall, and at least one fluid-guiding fitting communicating with said fluid-guiding passage;
    an illumination optical fiber bundle extending from the operation section through the protective tube to penetrate the connector body axially thereof; and
    at least one fluid-guiding tube extending from the operation section through the protective tube to penetrate the connector body axially thereof for connection to said fluid-guiding passage, the improvement wherein said connector further comprises:
    at least one annular grooved communication chamber formed in the outer peripheral wall of the connector body to communicate with the fluid-guiding passage; and
    a ring member which surrounds the annular grooved communication chamber and rotates along the outer peripheral wall of the connector body in a fluid tightness and which is provided with a fluid-guiding fitting.

2. The endoscope connector according to claim 1, wherein sealing means is provided between both edges of the annular grooved communication chamber of the connector body and the ring member.

3. The endoscope connector according to claim 2, wherein the sealing means comprises a pair of O-rings.

4. The endoscope connector according to claim 3, wherein the connector body has an annular groove formed in those portions of the outer peripheral wall of the connector body which lie adjacent to both edges of the communication chamber; and the O-ring is provided in the annular groove in contact with the inner wall of the ring member.

5. The endoscope connector according to claim 3, wherein a pair of annular flanges are formed on both edges of the ring member to project radially into the communication chamber; an annular groove is formed in each of the annular flanges; and the O-ring is set in the annular groove in contact with the inner wall of the communication chamber.

6. The endoscope connector according to claim 1, wherein a cock valve is provided in the fluid-guiding fitting.

7. The endoscope connector according to claim 1, wherein the ring member is provided with another fluid-guiding fitting communicating with the communication chamber.

8. The endoscope connector according to claim 7, wherein a cock valve is provided in the respective fluid-guiding fittings.

* * * * *